United States Patent [19]
Brotz

[11] Patent Number: 5,584,859
[45] Date of Patent: Dec. 17, 1996

[54] SUTURE ASSEMBLY

[76] Inventor: Gregory R. Brotz, P.O. Box 1322, Sheboygan, Wis. 53081

[21] Appl. No.: 492,237

[22] Filed: Jun. 19, 1995

Related U.S. Application Data

[63] Continuation-in-part of Ser. No. 134,659, Oct. 12, 1993, Pat. No. 5,425,747.

[51] Int. Cl.$^6$ ..................................................... A61B 17/04
[52] U.S. Cl. ........................... 606/228; 606/215; 606/230
[58] Field of Search ..................................... 606/214, 215, 606/216, 221, 224, 226, 230

[56] References Cited

U.S. PATENT DOCUMENTS

| | | | |
|---|---|---|---|
| 3,123,077 | 3/1964 | Alcamo | 606/228 |
| 4,467,805 | 8/1984 | Fukuda | 606/228 |
| 4,621,639 | 11/1986 | Transue et al. | 606/215 |
| 5,222,976 | 6/1993 | Yooh | 606/223 |
| 5,342,376 | 8/1994 | Ruff | 606/228 |

*Primary Examiner*—Gary Jackson
*Attorney, Agent, or Firm*—William Nitkin

[57] ABSTRACT

A suture assembly made of bioabsorbable material is disclosed having a central body member with a plurality of elongated lateral members in a plane extending perpendicularly on each side therefrom and interconnected to the central body member by elastic connectors, each lateral member having a plurality of barb members extending at an acute angle therefrom, for the lateral members to be inserted laterally into two sides of a cut in body tissue, stretching the elastic connectors so that after insertion the two sides of the cut are joined at the incision junction around or above the central body member and are retained securely and non-withdrawably in the body tissue by the barb members on such lateral members, with such lateral members and attached body tissue being pulled toward the central body member by the contracting action of the elastic connectors. Also disclosed is a method for utilizing the suture assembly of this invention.

9 Claims, 3 Drawing Sheets

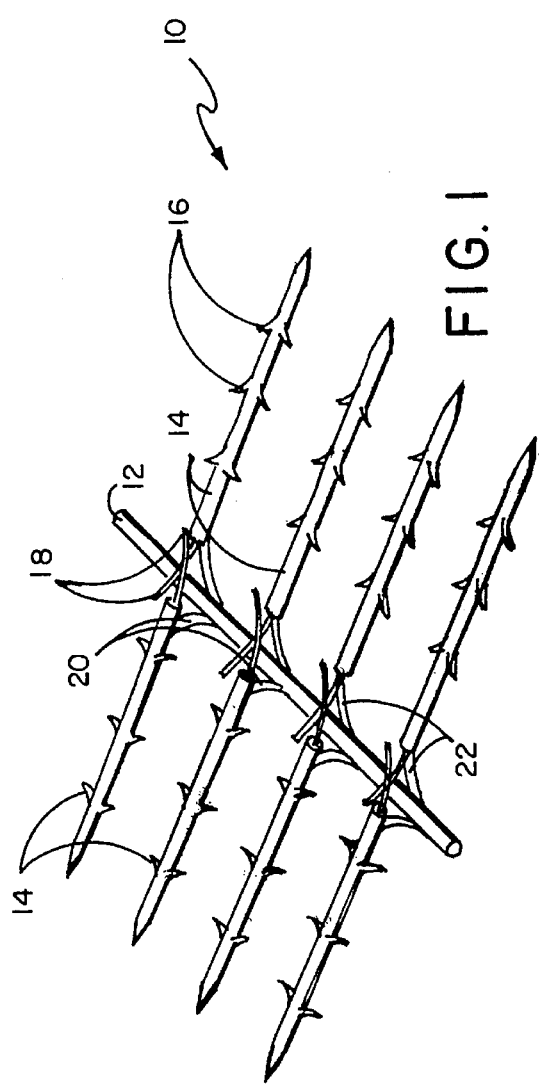
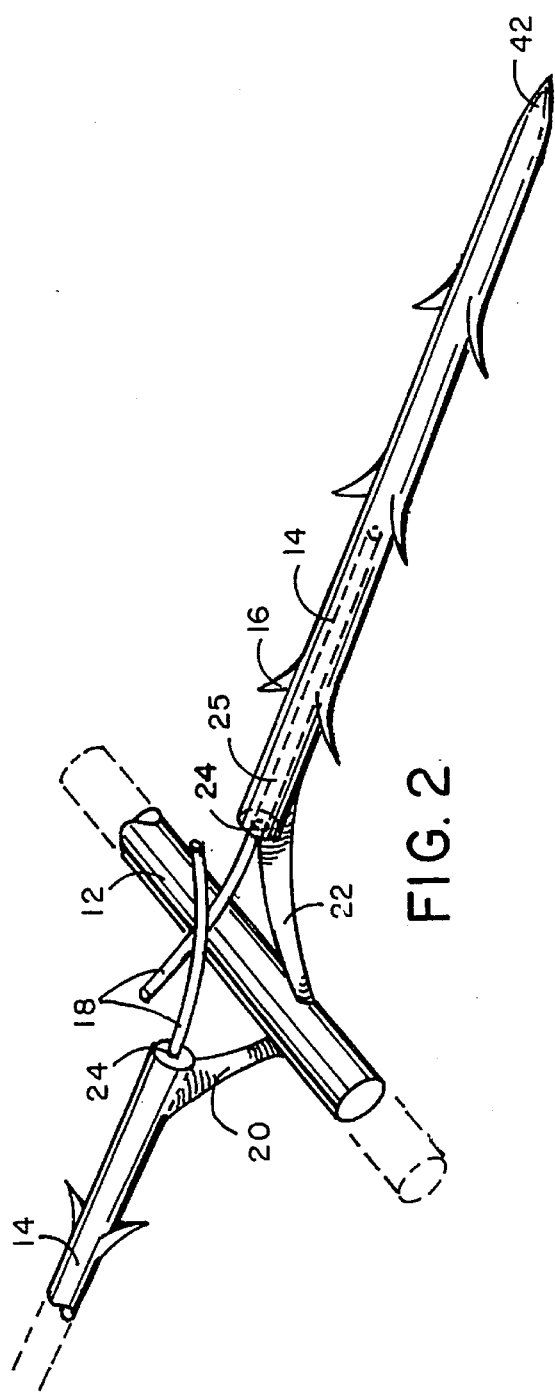

SUTURE ASSEMBLY

This application is a continuation-in-part of my previous application under the title Suture, Ser. No. 08/134,659 filed Oct. 12, 1993, now U.S. Pat. No. 5,425,747.

BACKGROUND OF THE INVENTION

1. Field of the Invention

The device of this invention resides in the area of sutures and fasteners for closing the two sides of an incision or cut in human skin or other body tissue and more particularly relates to a device having a central body member from which extend elastic connectors connecting to a plurality of lateral members with multiple barb members formed thereon which lateral members are inserted laterally into the two sides of a cut or incision to join the two sides together at a junction at the central body member.

2. Description of the Prior Art

Sutures for closing incisions or wounds are well known in the prior art. Such sutures or ligatures are often attached to the shank end of a needle and are utilized by physicians to make stitches to close incisions or wounds so that they may heal. Sutures are formed not only of thread-like material, but are also available as a one-piece unit combined with a needle. Sutures are available in a wide variety of monofilament and braided suture material. Sutures can be formed of non-absorbable material such as cat gut, silk nylon, polyester polypropylene, linen, or cotton as well as bioabsorbable synthetic material such as polymers and copolymers of glycolic and lactic acid. Germicides can also be incorporated into the structure of sutures which can be retained by the suture substrate to provide long-lasting germicidal properties.

Also known in the prior art are fasteners which eliminate the need for sutures in many instances. These fasteners are commonly referred to as "staples" and are useful in joining tissue layers laterally, for example, closing wounds in skin or fascia. Such staples are dispensed by implanting devices loaded with such surgical fasteners, the use of which devices can accomplish in very short time what would take many minutes to perform by suturing. Some staples can be made of bioabsorbable materials. The use of such fasteners results in a significantly reduced loss of blood and also lowers the level of trauma to the patient. Such staples can be in the form of metal staples which have arms bent by the fastening device to hook the separated body tissue together. Staples can require the stapling apparatus to have an anvil member which must be positioned under the tissue to be stapled so that the arms of the staple can be bent inwards. Two-part fastening devices also have been used which incorporate a barbed staple, the arms of which are attached to a bottom retaining member. One drawback to employing staples requiring a retainer member be attached to it is that there must be means for positioning such retainer member under the body tissue to be joined, and one must have access to the body tissue both from above and below the body tissue. Metal staples applied to the body must also be removed by staple extractors.

Other types of surgical fasteners include skin tacks which are used to join two sides of an incision. Such skin tacks include a barbed tip on each end of the inverted U-shaped tack, the body of which is transversely positioned across an incision or cut and the tack applied so that the barbed tips engage straight downward into the skin to hold each side of the adjacent layers of body tissue together. In such fastening devices no back retainer is required.

SUMMARY OF THE INVENTION

It is an object of this invention to provide an improved surgical fastener for joining skin or other body tissue such as separated by an incision.

The structure of this invention consists of a central body member having a plurality of lateral members attached thereto by elastic connectors on opposite sides, such lateral members being disposed in the same plane parallel to one another and perpendicular to the central body member. Disposed on each lateral member is a plurality of barb members which each extend therefrom at a rearwardly disposed acute angle to the direction of insertion. These lateral members, when inserted laterally into the skin or body tissue, remain fixed in position because the barb members, if the skin or body tissue is moved in a direction away from the central body member, will catch the skin or body tissue and prevent such outward movement. When the lateral members are inserted, the elastic connectors are stretched; and when the lateral members are positioned in the skin or body tissue and held in place by the barb members, the elastic connectors pull the lateral members toward the central body member thereby also pulling the body tissue to help close the cut or incision. In one embodiment of this invention each lateral members can have a bore defined along a portion of its length with an aperture at its inner end nearest the central body member in communication with the bore. A removable elongated rod-like insertion member can be inserted through the aperture and into the bore to aid in directing and pushing the lateral member into the skin or body tissue. After the suture is in its desired position, the insertion member can be pulled out of the bore in the lateral member. The structure of the suture assembly of this invention can be made of bioabsorbable material so that it will dissolve gradually as the cut or incision heals. Surgical adhesives based on collagen, fibrinogen or other formulations can also be used with the suture assembly of this invention. The insertion member can be made of plastic or any other equivalent stiff material. The lateral members and central body member can have an extremely narrow diameter, yet be stiff enough to be inserted into the skin or other tissue to be joined. The barb members can be disposed either in a plane parallel to the plane of the lateral members or, in an alternate embodiment, can be disposed not only parallelly but also perpendicularly to such plane or at other positions around the lateral members to provide for even greater retention of the suture assembly within the skin or body tissue into which the lateral members of the suture assembly of this invention are inserted.

BRIEF DESCRIPTION OF THE DRAWINGS

FIG. 1 illustrates a perspective view of one embodiment of the suture assembly of this invention showing the elastic connectors and insertion members.

FIG. 2 illustrates an enlarged perspective view of two of the lateral members of FIG. 1.

DESCRIPTION OF THE PREFERRED EMBODIMENT(S)

Figure 3:
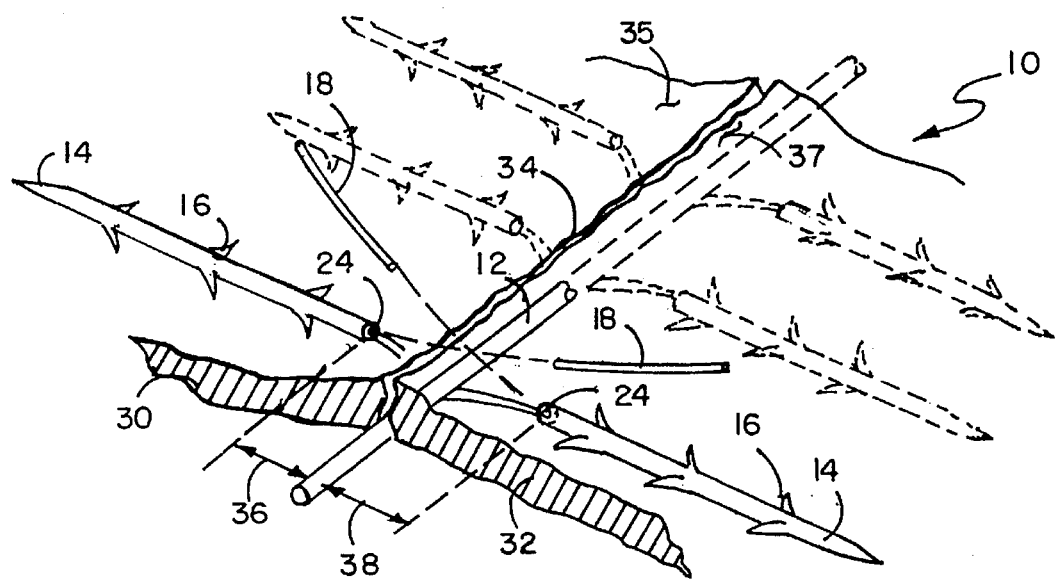
FIG. 3 illustrates a perspective view of the suture assembly of FIG. 1 having been inserted laterally into each side of a cut in skin.

FIG. 1 illustrates a perspective view of suture assembly 10 of one embodiment of this invention incorporating elastic connectors 20 and 22, each attached to an associated lateral member 14 and to central body member 12. In the embodiment shown elastic connectors 20 and 22 cause central body member 12 to be displaced below the level of the lateral members so that when the body tissue is closed thereover, the junction of the two sides of the cut in the body tissue is disposed above central body member 12 as will be described further below. This positioning of the suture assembly below the skin provides the advantage that nothing is disposed on the surface of the skin that might otherwise obstruct the adherence of any bandage placed over the cut. Elastic connectors 20 and 22 allow for the lateral members as seen in greater detail in FIG. 2, to be pushed deeply into the body tissue so as to stretch elastic connectors 20 and 22 beyond distances 36 and 38, seen in FIG. 3, such that when the lateral members are released from pressure pushing them into the tissue, the elastic connectors then pull the lateral members back toward the central body member. When this inward pulling occurs, barb members 16 on each lateral member engage into the body tissue and pull the body tissue with the lateral member such that the body tissue on both sides of the incision contact one another, which junction in the embodiment illustrated occurs above central body member 12. This additional inward force aids in the closure of the cut. Insertion members 18, as also seen in FIGS. 2 and 3, can be inserted into bores defined in each of the lateral members to aid in the manipulation, aiming and forcing of the lateral members into the tissue. Each insertion member 18 fits within its respective bore 25 through aperture 24. The insertion members can be made of thin, plastic, rod-like material. After the lateral member is pushed into the tissue with the aid of an insertion member and is in its desired position with its elastic connectors stretched, such as elastic connectors 20 and 22 seen in FIG. 2, the outward pressure is released by insertion member 18 being removed from bore 25 by pulling it completely out of bore 25 such that the lateral member is then free to be pulled by its respective elastic connector back toward the central body member. When the elastic connector is in its unstretched state, having pulled the body tissue or skin toward the central body member, a tissue junction is then created above the central body member.

Figure 9:
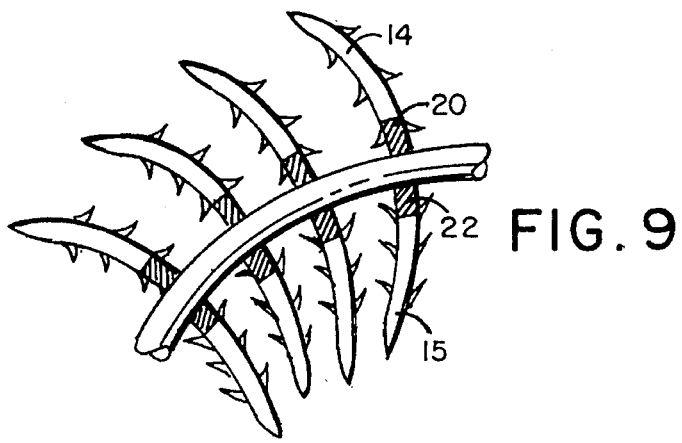
FIG. 9 illustrates a perspective view showing a curved central member.

FIG. 3 illustrates a perspective view of suture assembly 10 of this invention within incision 34 having first and second sides 35 and 37 about to be brought together over central body member 12. While most of the lateral members are shown in dashed lines, the two nearest the viewer are shown in solid lines to better illustrate them. Although a surgical incision is illustrated, the suture assembly of this invention can also be used to fasten the irregular sides of a cut or accidental wound. The central member can be flexible to bend to accommodate any irregularities in the shape of the cut. The suture of this invention is shown substantially enlarged in this view, but its size can vary depending on several factors such as the extent of the cut, the type of tissue to be joined, the location of the cut, etc. The suture assembly can be made of bioabsorbable material which is well known in the prior art and should have sufficient stiffness so as to be able to be laterally inserted into the skin or body tissue. Surgical adhesives can also be used to aid in holding the lateral members in position and in closure of the cut or incision. In all embodiments of the suture assembly of this invention, central body member 12 and lateral members 14 can be of any desired length. The central and lateral members can be cut to any length or can be packaged in a variety of pre-cut lengths and in pre-shaped curves as seen in FIG. 9. As seen in FIG. 1, central body member 12 has a plurality of laterally extending lateral members 14. Other lateral members can extend from the sides of central body member 12, where the central body member and lateral members in this embodiment are not all in the same general plane. Disposed along each lateral member are a plurality of barb members 16. The barb members can be either molded in a barb-like shape or can be formed from acute angular cuts made directly in the bioabsorbable material of the lateral members with such cut portions pushed outward and separated away from the lateral member. The barb members, in one embodiment, can be formed parallel to the plane of the lateral members.

In use, second side 37 of the incision is manually held while the lateral members on this side of the central body member are inserted laterally into second side 37, stretching the elastic connectors, such as elastic connector 22 seen in FIG. 2. A removable insertion member 18 can be inserted through aperture 24 into bore 25 in lateral member 14 to help direct and position lateral member 14 into the second side of the cut. When each lateral member is in position and held by its barb members 16, insertion member 18 can be pulled out of aperture 24 at the end of bore 25 in lateral member 14, as seen in FIG. 2, allowing elastic connector 22 to then pull lateral member 14 toward central body member 12 to help close the cut. Then first side 35 is held while the lateral member of the opposite side of the cut is similarly inserted laterally into the first side, stretching its elastic connector with the next step being to remove the insertion member 18 for the elastic connector to urge first side 35 toward the central body member to form an incision junction at central body member 12, which sides are held in place by the plurality of barb members which resist outward movement of the skin or body tissue away from the central body member and also by the inward tension of the elastic members. Other barb members can be formed or positioned on the lateral members perpendicular or at other angles to the plane of the lateral members. The lateral members can be rounded and have pointed ends 42 to facilitate their lateral insertion into the skin or body tissue.

Figure 4:
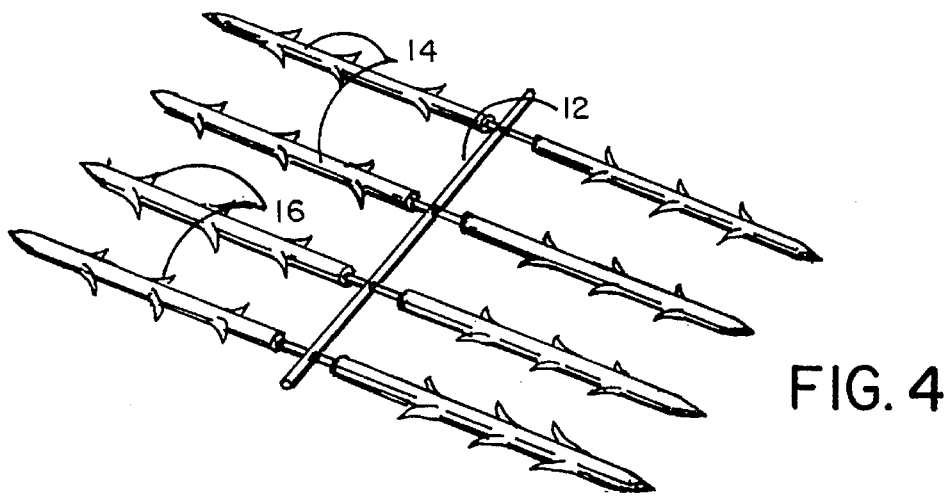
FIG. 4 illustrates a perspective view of another embodiment of the suture assembly of this invention showing the elastic connectors in a stretched state.
Figure 5:
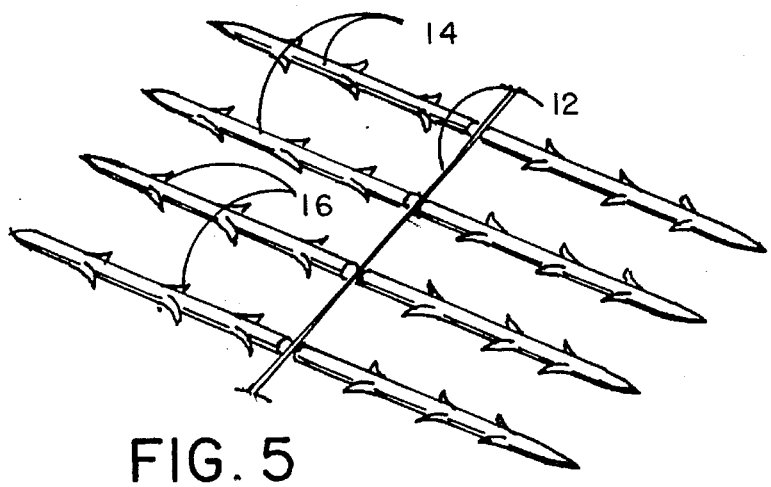
FIG. 5 illustrates a perspective view of the suture assembly of FIG. 4 with the elastic connectors in an unstretched, relaxed state.

FIG. 4 illustrates an alternate embodiment wherein each lateral member 14 is connected directly by an elastic connector, in this case being stretched elastic connector 40, to central body member 12 without an insertion member. The lateral members are pushed directly into the body tissue on both sides of the central body member, stretching the elastic connectors to a stretched state as seen in FIG. 4. In FIG. 5 the elastic connectors 40 have contracted into an unstretched state such that the lateral members 14 are now disposed adjacent to the central body member 12 in the same plane as the plane of central body member 12. In this view the elastic connectors are not visible since they have contracted significantly, thereby pulling the lateral members almost against central body member 12.

Figure 6:
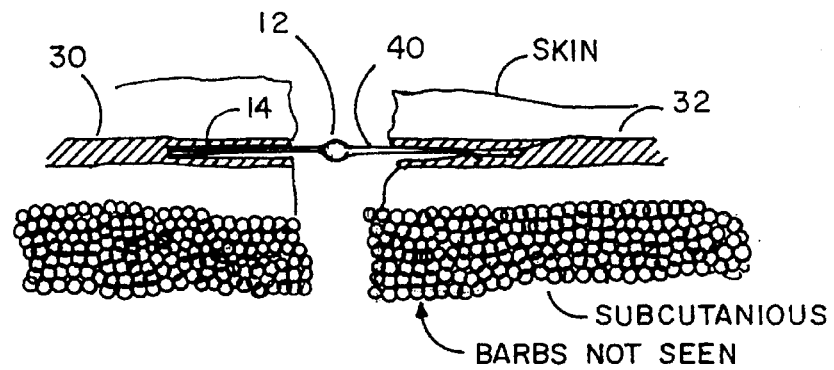
FIG. 6 illustrates a cross-sectional end view of the suture assembly of FIG. 4 showing the elastic members being stretched.
Figure 7:
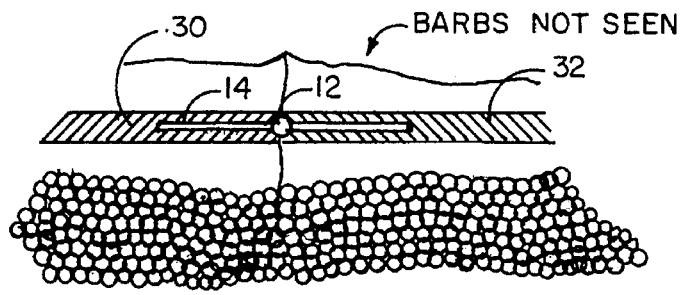
FIG. 7 illustrates a cross-sectional end view of FIG. 5 showing the elastic members in a relaxed state.

In FIG. 6, which is a cross-sectional end view of the embodiment of FIG. 4, elastic connectors 40 are stretched while lateral members 14 are inserted into the tissue of first and second sides 30 and 32 of the incision. Upon release of outward pressure, as seen in FIG. 7, the elastic connectors contract, pulling the lateral members inward to be adjacent to central body member 12 such that the elastic connectors, being contracted, are no longer visible and have pulled the tissue on first and second sides 30 and 32 together over and around bioabsorbable central body member 12.

Figure 8:
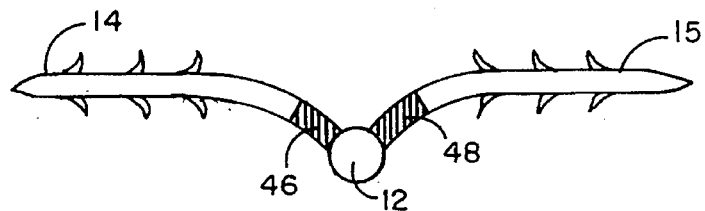
FIG. 8 illustrates a cross-sectional view showing prestressed lateral members.

In some cases where it is not desirable for central body member 12 to be positioned in the same plane as its lateral members, the central body member can be positioned below such plane, as illustrated in FIGS. 2 and 8, where the lateral members each are attached by elastic connectors disposed at an angle along an edge of their inner end, thereby positioning the central body member below the level of the incision junction. The central member, when positioned lower as seen in FIG. 8, can be elastic, flexible, semi-rigid or rigid depending on the location of the incision and the stress and movement that might occur in relation to the incision. Lateral members 14 and 15 and elastic connectors 46 and 48, as seen in FIG. 8, can be pre-stressed to curve upwards to help the tissue inserted thereover to be drawn together.

Although the present invention has been described with reference to particular embodiments, it will be apparent to those skilled in the art that variations and modifications can be substituted therefor without departing from the principles and spirit of the invention.

I claim:

1. A suture assembly for lateral insertion in body tissue having a cut defined therein forming first and second sides of said cut, said suture assembly for joining said first and second sides of said cut at a junction, comprising:

a central body member having first and second sides and first and second ends;

a plurality of lateral members each having a length, an inner end and an outer end, said lateral members disposed perpendicularly to said central body member adjacent to said first and second sides of said central body member, said lateral members being in parallel and planar relationship to one another, each lateral member for direct insertion into a side of said cut;

a plurality of barb members positioned on said lateral members, each extending at an acute angle to its associated lateral member, said barb members preventing outward movement of said body tissue surrounding said lateral members away from said central body member after said lateral insertion of said lateral members into said first and second sides of said cut and positioning said central body member at said junction of said first and second sides of said cut; and means on said body to urge each lateral member toward said central body member.

2. The suture assembly of claim 1 wherein said means to urge each lateral member toward said central body member comprises an elastic connector attached between a respective lateral member and said central body member, said elastic connector being stretchable during insertion of said lateral member into said body tissue and when returning to an unstretched state, pulling said body tissue toward said central body member.

3. The suture assembly of claim 2 wherein each elastic connector is disposed at an angle to the plane of its respective lateral member to position said central body member below the level of the plane of said lateral member.

4. The suture assembly of claim 2 further including:

an insertion member associated with each of said lateral members; and means to releasably engage each of said insertion members, respectively, to its associated lateral member.

5. The suture assembly of claim 3 further including:

an insertion member associated with each of said lateral members; and means to releasably engage each of said insertion members, respectively, to its associated lateral member.

6. The suture assembly of claim 4 wherein said means to releasably engage said insertion member to its associated lateral member comprises:

a bore defined at said inner end of said lateral member and extending along a portion of said length of said lateral member; and wherein said insertion member is an elongated rod-like member releasably positionable in said bore.

7. The suture assembly of claim 5 wherein said means to releasably engage said insertion member to its associated lateral member comprises:

a bore defined at said inner end of said lateral member and extending along a portion of said length of said lateral member; and wherein said insertion member is an elongated rod-like member releasably positionable in said bore.

8. The method of joining at a junction first and second sides of a cut defined in body tissue, comprising the steps of:

providing a suture assembly made of bioabsorbable material having a central body member having first and second sides, a plurality of lateral members disposed perpendicularly to said central body member on each side of said central body member, said lateral members in parallel and planar relationship to one another, said lateral members each having an inner end, and a plurality of barb members positioned on said lateral members, each extending at an acute angle to said lateral member;

providing an elastic connector associated with each lateral member, said elastic connector attached between said central body member and said inner end of said lateral member;

laterally inserting said lateral members positioned along said first side of said central body member into said first side of said cut and thereby stretching said elastic connectors attached thereto;

laterally inserting said lateral members positioned along said second side of said central body member into said second side of said cut and thereby stretching said elastic connectors attached thereto;

engaging the body tissue of said first and second sides of said cut by said positioning of said barb members thereagainst;

preventing outward movement of said first and second sides of said cut away from said central body member by said engagement of said barb members against the body tissue of said first and second sides of said cut; and providing inward force of said lateral members toward said junction at said central body member by inward contraction of elastic connectors.

9. The method of claim 8 further including the steps of:

providing an insertion member associated with each of said lateral members; and providing means to releasably engage each of said insertion members, respectively, to its associated lateral member.

\* \* \* \* \*